United States Patent [19]

Leong et al.

[11] Patent Number: 5,486,625
[45] Date of Patent: Jan. 23, 1996

[54] PROCESS FOR THE PREPARATION OF CHIRAL INTERMEDIATES USEFUL FOR THE SYNTHESIS OF ANTIFUNGAL AGENTS

[75] Inventors: William Leong, Westfield; Lyman H. Smith, Piscataway, both of N.J.

[73] Assignee: Schering Corporation, Kenilworth, N.J.

[21] Appl. No.: 272,411

[22] Filed: Jul. 8, 1994

[51] Int. Cl.$^6$ .................. C07D 317/00; C07D 249/08; C07D 233/04
[52] U.S. Cl. .................. 549/448; 549/296; 548/268.8; 548/315.4
[58] Field of Search .................. 549/296, 448; 548/268.8, 315.4

[56] References Cited

U.S. PATENT DOCUMENTS

| | | | |
|---|---|---|---|
| 4,619,931 | 10/1986 | Heeres et al. | 544/366 |
| 4,791,111 | 12/1988 | Heeres et al. | 544/366 |
| 4,818,758 | 4/1989 | Kampe et al. | 544/366 |
| 4,877,878 | 10/1989 | Kampe et al. | 544/366 |
| 5,039,676 | 8/1991 | Saksena et al. | 514/254 |

FOREIGN PATENT DOCUMENTS

| | | | |
|---|---|---|---|
| 253166 | 1/1988 | European Pat. Off. | 544/366 |
| 402989 | 12/1990 | European Pat. Off. | 544/366 |
| 539938 | 5/1993 | European Pat. Off. | 544/366 |
| 2053780 | 2/1990 | Japan | 544/366 |
| WO89/04829 | 6/1989 | WIPO. | |
| WO93/09114 | 5/1993 | WIPO. | |
| 9319061 | 9/1993 | WIPO | 544/366 |
| PCT/US94/04355 | 4/1994 | WIPO. | |

OTHER PUBLICATIONS

Seebach, et al., *Helv. Chim. Acta*, 63, 197–200 (1980).
Wu, et al., *J. Org. Chem.*, 58, 3586–3588 (1993).
Aebi, et al., *Lieb. Ann. Chem.*, 2114–2126 (1983).
Seebach, et al., *Org. Syn.*, 63, 109–121 (1985).
Kartha, *Tet. Lett.*, 27, (No. 29) 3415–3416 (1986).
Weber, et al., *Angew. Chem. Int. Ed. Engl.*, 31, (No. 1) 84–86 (1992).
Baldwin, et al., *Tetrahedron*, 46, 4733–4748 (1990).
Harmange, et al., *Tet. Asymm.*, 4, (No. 8) 1711–1754 (1993).
Bennett, et al., *Tet. Lett.*, 33, (No. 43) 6507–6510 (1992).
Tang, et al., *Tet Lett.*, 33, (No. 37) 5299–5302, 5303–5306 (1992).
Dehmlow, et al., *Tet Lett.*, 33, (No. 25) 3607–3610 (1992).
Craig, et al., *Tet Lett.*, 33, (No. 5) 695–698 (1992).
Marek, et al., *Tet. Lett.*, 33, (No. 13) 1747–1748 (1992).
Srebnik, et al., *J. Chem. Soc., Chem. Comm.*, 1070–1071 (1984).
Hosokowa, et al., *Tet. Lett.*, (No. 21) 1821–1824 (1976).
Bravo, et al., *J. Med. Chem.*, 35, 3102–3110 (1992).

*Primary Examiner*—Cecilia Tsang
*Attorney, Agent, or Firm*—Paul A. Thompson

[57] ABSTRACT

Described is a process for preparing chiral compounds of the formula

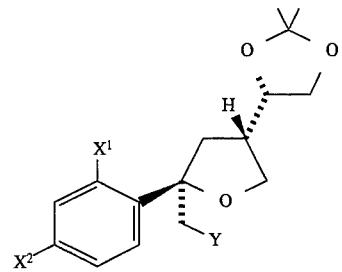

wherein $X^1$ and $X^2$ are independently F or Cl, and Y is Cl, Br or I, comprising reacting a triol of the formula

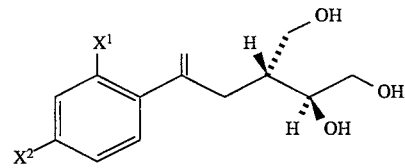

wherein $X^1$ and $X^2$ are as defined above, with acetone in the presence of a catalyst, then with a halogen selected from $Cl_2$, $Br_2$ or $I_2$, or N-bromosuccinimide or N-iodosuccinimide.

17 Claims, No Drawings

PROCESS FOR THE PREPARATION OF CHIRAL INTERMEDIATES USEFUL FOR THE SYNTHESIS OF ANTIFUNGAL AGENTS

BACKGROUND OF THE INVENTION

The present invention comprises a process for preparing chiral intermediates useful in the preparation of tri-substituted tetrahydrofuran triazole or imidazole antifungals.

PCT International Publication No. WO 69/04829, U.S. Pat. No. 5,039,676, and PCT International Publication No. WO 93/09114 disclose substituted tetrahydrofuran azole and imidazole compounds having utility as antifungal agents. A number of processes for the synthesis of these compounds are known.

PCT International Application No. PCT/US92/08981 discloses a process for the synthesis of tri-substituted tetrahydrofuran azole antifungals via a tosylate intermediate of the formula

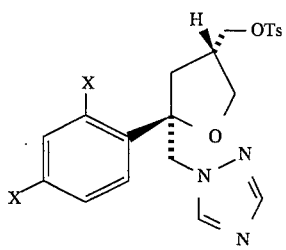

wherein X is both F or both Cl or one X is F and the other is Cl.

PCT International Application No. PCT/US94/04355 describes a process for preparing chiral intermediates of the formula (I)

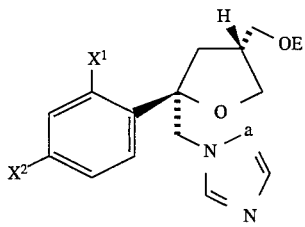

wherein: a is CH or N; $X^1$ and $X^2$ are independently F or Cl; and E is —$SO_2R^6$, wherein $R^6$ is $C_1$–$C_6$ alkyl, aryl, substituted aryl or —$CF_3$. Compounds of the formula (1) are useful as intermediates in the preparation of tetrahydrofuran azole or imidazole antifungal agents.

SUMMARY OF THE INVENTION

The present invention provides a process for preparing chiral compounds of the formula (II)

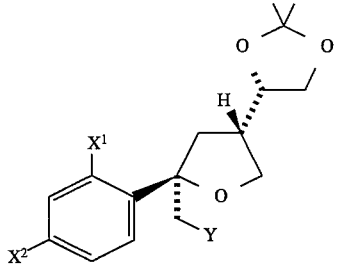

wherein $X^1$ and $X^2$ are independently F or Cl, and Y is Cl, Br or I. The process of the present invention comprises reacting a triol of the formula

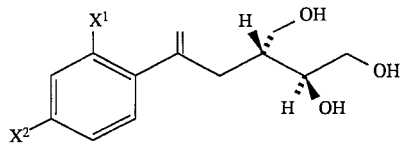

wherein $X^1$ and $X^2$ are as defined above, with acetone in the presence of a catalyst, then with a halogen selected from $Cl_2$, $Br_2$ or $I_2$, or with NBS or NIS, to form a compound of formula (II).

Preferably the catalyst is $I_2$.

The present invention also provides a process for preparing a compound of the formula (II) comprising the steps:

(a) using a nonaqueous base to deprotonate a chiral compound of the formula

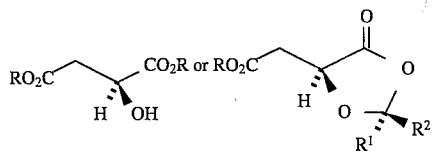

wherein: R is $C_1$–$C_6$ alkyl;

one of $R^1$ or $R^2$ is H and the other is —$C(CH_3)_3$ or —$CCl_3$, or $R^1$ and $R^2$ are both $C_1$–$C_6$ alkyl, or $R^1$ and $R^2$ together with the carbon to which they are attached comprise a 6-membered carbocyclic ring, then treating with a compound of the formula

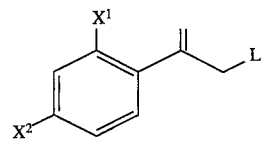

wherein $X^1$ and $X^2$ are as defined above and L is a leaving group, to form a chiral compound of the formula

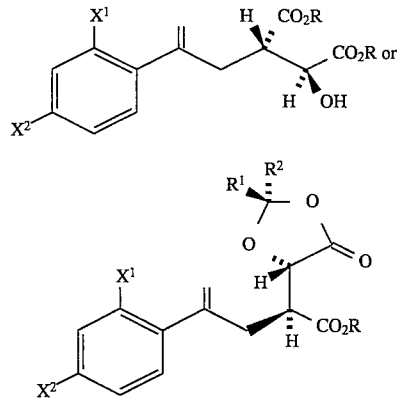

respectively, wherein $X^1$, $X^2$, R, $R^1$ and $R^2$ are as defined above;

(b) reducing the product of step (a) with a hydride reducing agent to form a chiral triol of the formula

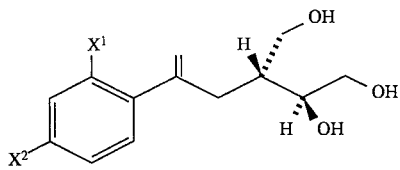

wherein $X^1$ and $X^2$ are as defined above; and (c) reacting the triol of step (b) with acetone in the presence of a catalyst, then with a halogen selected from $Cl_2$, $Br_2$ or $I_2$, or with NBS or NIS, to form a chiral compound of formula (II).

The present invention further provides a process for converting a compound of the formula (II) to a compound of the formula (I)

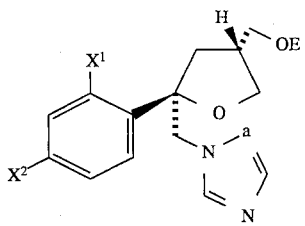

wherein: a is CH or N; $X^1$ and $X^2$ are independently F or Cl; and E is $-SO_2R^6$, wherein $R^6$ is $C_1-C_6$ alkyl, aryl, substituted aryl or $-CF_3$, comprising the steps:

(d) treating a compound of formula (II) with an alkali metal triazole or imidazole to form a chiral compound of the formula

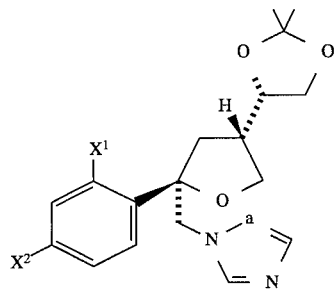

wherein a, $X^1$ and $X^2$ are as defined above;

(e) hydrolyzing the product of step(d) with an aqueous acid to form a diol intermediate of the formula

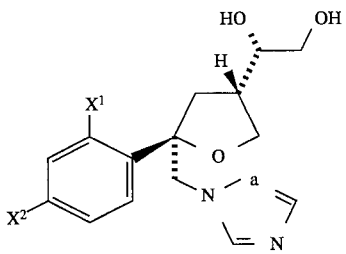

followed by oxidatively cleaving the diol using $H_5IO_6$, $NaIO_4$ or $Pb(OAc)_4$ to form an aldehyde of the formula

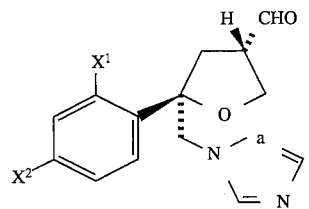

wherein a, $X^1$ and $X^2$ are as defined above;

(f) reducing the aldehyde of step (e) with a hydride reducing agent to form an alcohol of the formula

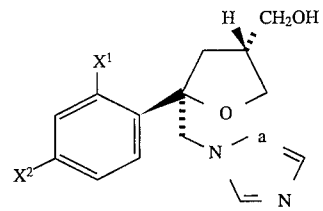

wherein a, $X^1$ and $X^2$ are as defined above; and (g) treating the alcohol of step (f) with a compound of the formula E-X, wherein X is Cl or Br, and E is as defined above, to form a compound of formula (I).

In an alternative embodiment, the present invention provides a process for preparing a compound of the formula (III)

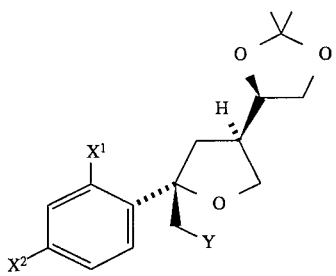

Compounds of the formula (III) are enantiomers of compounds of the formula (II). In this embodiment the process of the present invention comprises the steps:

(ai) using a nonaqueous base to deprotonate a chiral compound of the formula

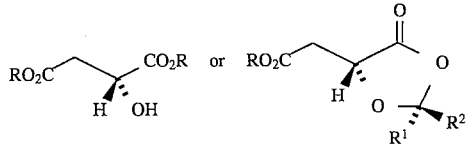

wherein: R is $C_1-C_6$ alkyl;
one of $R^1$ or $R^2$ is H and the other is $-C(CH_3)_3$ or $-CCl_3$, or $R^1$ and $R^2$ are both $C_1-C_6$ alkyl, or $R^1$ and $R^2$ together with the carbon to which they are attached comprise a 6-membered carbocyclic ring, then treating with a compound of the formula

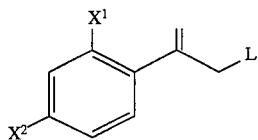

wherein $X^1$ and $X^2$ are as defined above and L is a leaving group, to form a chiral compound of the formula

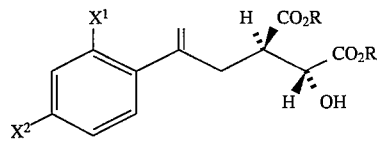

or

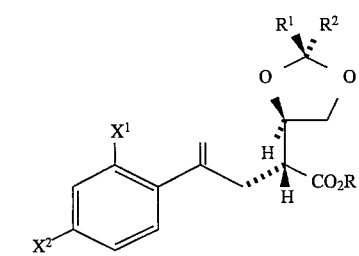

respectively, wherein $X^1$, $X^2$, R, $R^1$ and $R^2$ are as defined above; and
(bi) reducing the product of step (ai) with a reducing agent to form a chiral triol of the formula

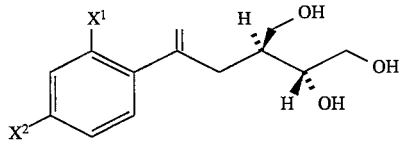

wherein $X^1$ and $X^2$ are as defined above; and
(ci) reacting the triol of step (bi) with acetone in the presence of a catalyst, then with a halogen selected from $Cl_2$, $Br_2$ or $I_2$, or with NBS or NIS, to form a chiral compound of formula (III).

In this embodiment, the present invention further comprises a process for converting a compound of the formula (III) to an enantiomer of a compound of formula (I), i.e., a compound of the formula (IV)

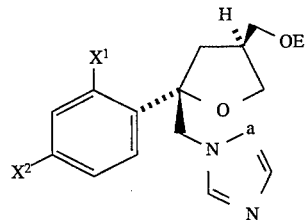

wherein: a is CH or N; $X^1$ and $X^2$ are independently F or Cl; and E is $-SO_2R^6$, wherein $R^6$ is $C_1-C_6$ alkyl, aryl, substituted aryl or $-CF_3$, comprising the steps:
(di) treating a compound of formula (III) with an alkali metal triazole or imidazole to form a chiral compound of the formula

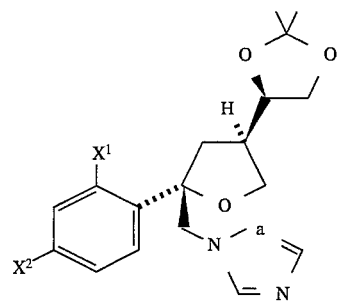

wherein a, $X^1$ and $X^2$ are as defined above;
(ei) hydrolyzing the product of step(di) with an aqueous acid to form a diol intermediate of the formula

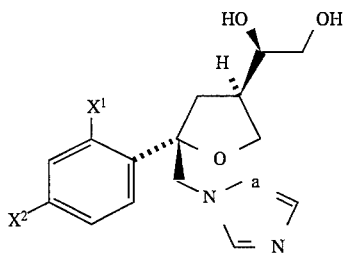

followed by oxidatively cleaving the diol using $H_5IO_6$, $NaIO_4$ or $Pb(OAc)_4$ to form an aldehyde of the formula

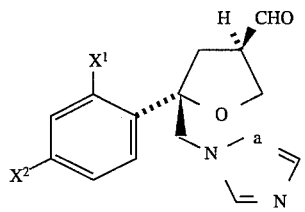

wherein a, $X^1$ and $X^2$ are as defined above;
(fi) reducing the aldehyde of step (ei) with a hydride reducing agent to form an alcohol of the formula

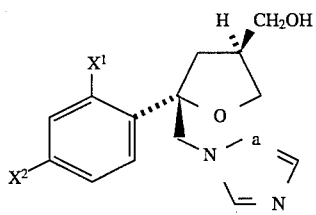

wherein a, $X^1$ and $X^2$ are as defined above; and
(gi) treating the alcohol of step (fi) with a compound of the formula E-X, wherein X is Cl or Br, and E is as defined above, to form a compound of formula (IV).

DETAILED DESCRIPTION

As used herein, the term:
"alkyl" means a straight or branched alkyl chains of 1 to 6 carbon atoms;
"aryl" means a $C_6-C_{10}$ carbocyclic aromatic group, such as phenyl or naphthyl; and "substituted aryl" means an aryl group having 1 to 3 substituents selected from halogeno, $C_1-C_6$ alkyl, $NO_2$ or $CF_3$;

"halogeno" means Cl, Br or I;

"leaving group" means a substituent which is readily displaced by a nucleophile, such as Cl, Br, I or —OSO$_2$R$^6$, wherein R$^6$ is C$_1$–C$_6$ alkyl, aryl, substituted aryl or —CF$_3$;

"hydride reducing agent" means LiAlH$_4$, NaBH$_4$, LiBH$_4$, NaBH$_3$CN, or a combination of NaBH$_4$ and LiCl;

"catalyst" means a reagent capable of catalyzing the reaction of acetone with the chiral triols of steps (b) and (bi) to form a cyclic ketal group, and is preferably iodine;

"acid catalyst" means a Lewis acid, such as BF$_3$·OEt$_2$, or protic acid, such as p-TSA or H$_2$SO$_4$, capable of catalyzing the reaction between a ketone or aldehyde and malic acid to form compound of the general formula

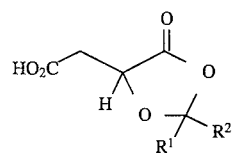

as described herein;

"aqueous acid" means an aqueous solution of an acid, such as HCl;

"alkali metal triazole or imidazole" means an alkali metal salt of the anion derived from triazole or imidazole, respectively, e.g., sodium triazole, potassium triazole, lithium triazole, sodium imidazole, potassium imidazole or lithium imidazole;

"base" means a basic compound capable of deprotonating a carboxylic acid and catalyzing an esterification reaction, including moderate bases, hydroxide bases, tertiary amine bases, Bu$_4$NOH and Bu$_4$NF.

"moderate base" means Na$_2$CO$_3$, Li$_2$CO$_3$ or K$_2$CO$_3$;

"hydroxide base" means an alkali metal hydroxide, such as NaOH, KOH, LiOH;

"tertiary amine base" means bases such as pyridine, DMAP, Et$_3$N and Hünigs base;

"nonaqueous base" means a non-nucleophilic reagent capable of generating a carbanion, such as LiN[Si(CH$_3$)$_3$]$_2$, NaN[Si(CH$_3$)$_3$]$_2$, KN[Si(CH$_3$)$_3$]$_2$, KN[CH(CH$_3$)$_2$]$_2$, NaN[CH(CH$_3$)$_2$]$_2$ or LiN[CH(CH$_3$)$_2$]$_2$; and "organic water miscible solvent" means an organic solvent which is soluble in water, and which is suitable for use with hydride reducing agents, such solvents including THF or C$_1$–C$_6$ alkanols, such as MeOH, EtOH and iPrOH.

As used herein the following reagents and solvents are identified by the abbreviations indicated: methanol (MeOH); tetrahydrofuran (THF); diethyl ether (Et$_2$O); t-butyl methyl ether (TBME); lithium di-isopropylamide (LDA); triethylamine (Et$_3$N); di-isopropylethylamine (Hünigs base); ethyl acetate (EtOAc); ethanol (EtOH); N,N-dimethylformamide (DMF); lithium hexamethyldisilazide (LiHMDS); 4-dimethylaminopyridine (DMAP); p-toluenesulfonyl chloride (tosyl chloride or TsCl); methanesulfonyl chloride (mesyl chloride or MsCl); p-toluenesulfonic acid (p-TSA); tetrabutylammonium hydroxide (Bu$_4$NOH); tetrabutylammonium fluoride (Bu$_4$NF); trimethylsilyltriflate (TMSOTf); (R)-(+)-α-methoxy-α-(trifluoromethyl)phenylacetyl chloride ((R)-MTPACl); lead tetraacetate (Pb(OAc)$_4$); N-bromosuccinimide (NBS); N-iodosuccinimide (NIS).

The present invention comprises a process for preparing a compound of the formula (II) and for converting the compound of formula (II) into a compound of the formula (I), as shown in Reaction Scheme 1.

Reaction Scheme 1

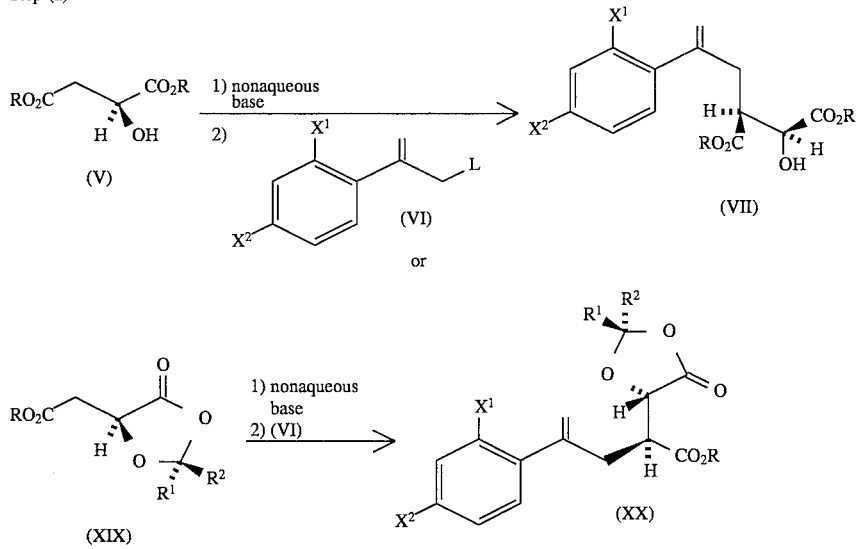

-continued
Reaction Scheme 1

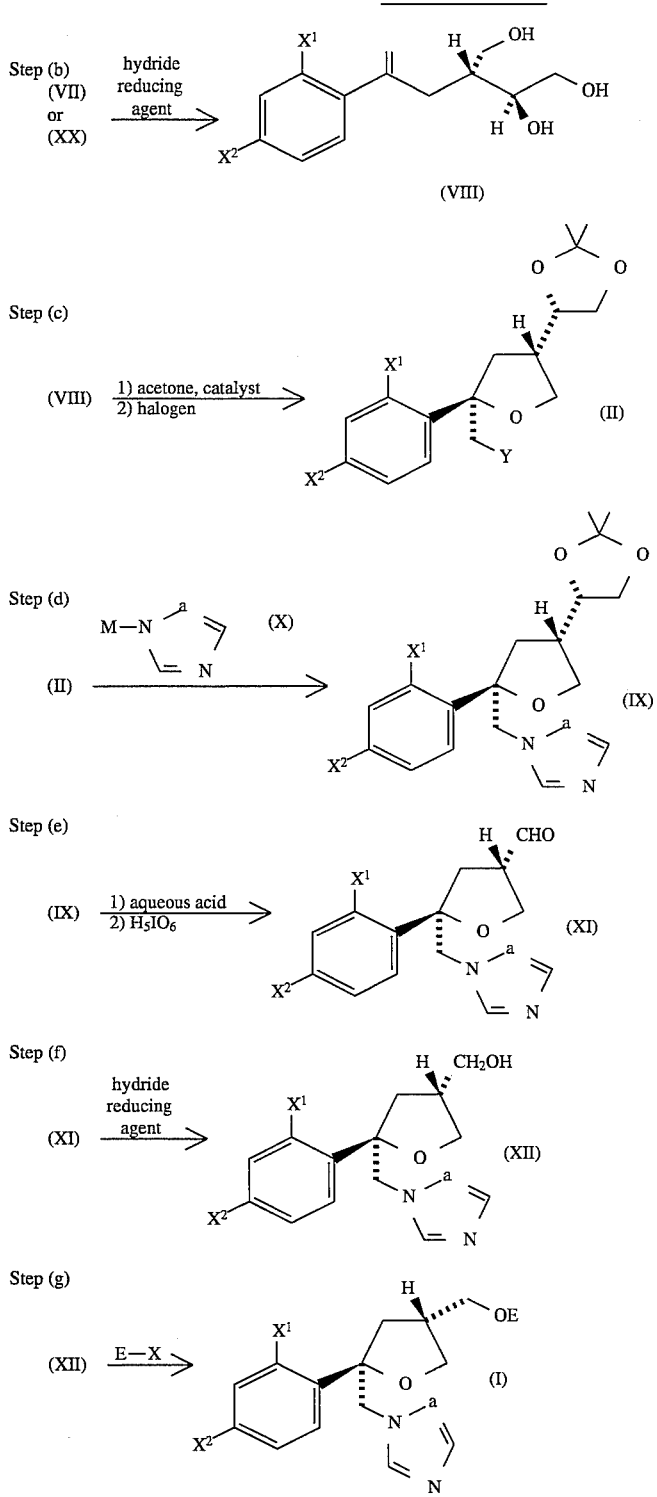

In Step (a) of Reaction Scheme 1, a diester of L-malic acid (V) wherein R is $C_1$–$C_6$ alkyl, or a L-malic acid derivative of the formula (XIX) wherein R, $R^1$ and $R^2$ are as defined above, is deprotonated by treating with a nonaqueous base, such as LiHMDS, in a suitable solvent, such as THF, at −100° to 0° C., preferably at −80° C. to −20° C., and the resulting anion reacted with a compound of the formula (VI), wherein $X^1$, $X^2$ and L are as defined above, at −100° to 0° C., preferably at −80° C. to −10° C., then quenched with $KH_2PO_4$ (aqueous) and extracted with an organic solvent, such as EtOAc, to give the product (VII) or (XX), respectively.

In Step (b), compound (VII) or (XX) is treated with a hydride reducing agent, such as $LiBH_4$ or a mixture of $NaBH_4$ and LiCl, in a suitable solvent, such as an organic water miscible solvent, preferably THF, MeOH, EtOH or iPrOH, and optionally in the presence of water, at −30° to 50° C., preferably at −10° to 30° C., and most preferably at 0° to 25° C., to give the triol product (VIII). When using a more reactive hydride reducing agent, such as $LiAlH_4$, the reaction is carried out under anhydrous conditions in an organic solvent such as THF or $Et_2O$.

In Step (c), the triol (VIII) is reacted with acetone and a catalyst, such as a catalytic amount of $I_2$, at 0° to 50° C., preferably at 10° to 30° C., and most preferably at about 25° C. The reaction mixture is treated with a halogen, preferably $I_2$, and a moderate base, such as $Na_2CO_3$, or alternatively with NBS or NIS, at −50° to 25° C., preferably about −30° to 0° C., then quenched with a mixture of $Na_2S_2O_3$, water and a moderate base, such as $K_2CO_3$, and extracted with an organic solvent, such as EtOAc to give a compound of the formula (II).

In Step (d), a compound of formula (II) is treated with an alkali metal triazole or imidazole of formula (X), wherein M is an alkali metal selected from Li, Na or K, and a is as defined above, at 50° to 150° C., preferably at 80°–120° C., and most preferably at 100°–110° C., in a suitable solvent, such as DMSO or DMF, to give the product (IX:).

In Step (e), a compound (IX) is hydrolyzed by treating with an aqueous acid, such as aqueous HCl, and a suitable solvent, such as THF at 0° to 50° C., preferably at 20° to 30° C., then treated with $H_5IO_6$, $NaIO_4$ or $Pb(OAc)_4$, at 0° to 50° C., preferably at 20° to 30° C., then quenched with a mixture of $Na_2S_2O_3$, water and a moderate base, such as $K_2CO_3$, and extracted with an organic solvent, such as EtOAc, to give the aldehyde (XI).

In Step (f), the aldehyde (XI) is treated with a hydride reducing agent, such as $NaBH_4$, in a suitable solvent, such as an organic water miscible solvent, preferably THF, MeOH, EtOH or iPrOH, preferably MeOH or iPrOH, at −30° to 50° C., preferably at −10° to 30° C., and most preferably at 0° to 25° C., to give an alcohol of the formula (XII). When using a more reactive hydride reducing agent, such as $LiAlH_4$, the reaction is carried out under anhydrous conditions in an organic solvent such as THF or $Et_2O$.

In Step (g), the alcohol (XII) is treated with a compound of the formula E-X, wherein X is Cl or Br, preferably Cl, and E is as defined above, preferably $-SO_2C_6H_4CH_3$ or $-SO_2C_6H_4Cl$, in the presence of a base and a suitable solvent to form a compound of the formula (I). Where the base is a hydroxide base, such as NaOH, the solvent is preferably THF, and where the base is a tertiary amine base, such as pyridine, the solvent is preferably $CH_2Cl_2$.

In an alternative embodiment the present invention comprises a process for preparing an enantiomer of a compound (II), e.g. a compound of the formula (III), and for converting compound (III) to an enantiomer of compound (I), e.g. a compound of the formula (IV), as shown in Reaction Scheme 2.

Reaction Scheme 2

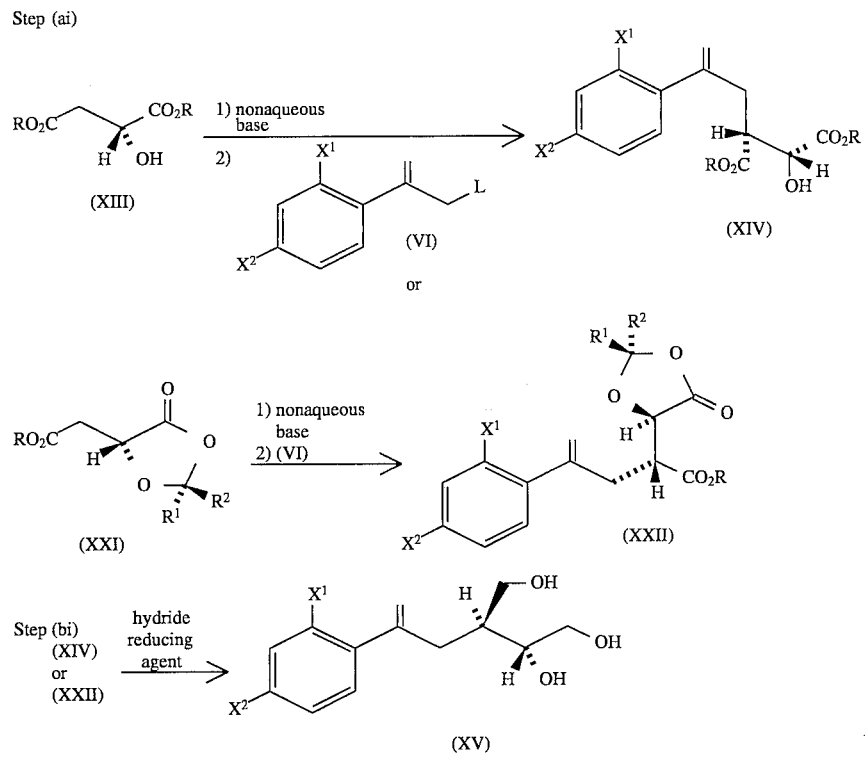

-continued
Reaction Scheme 2

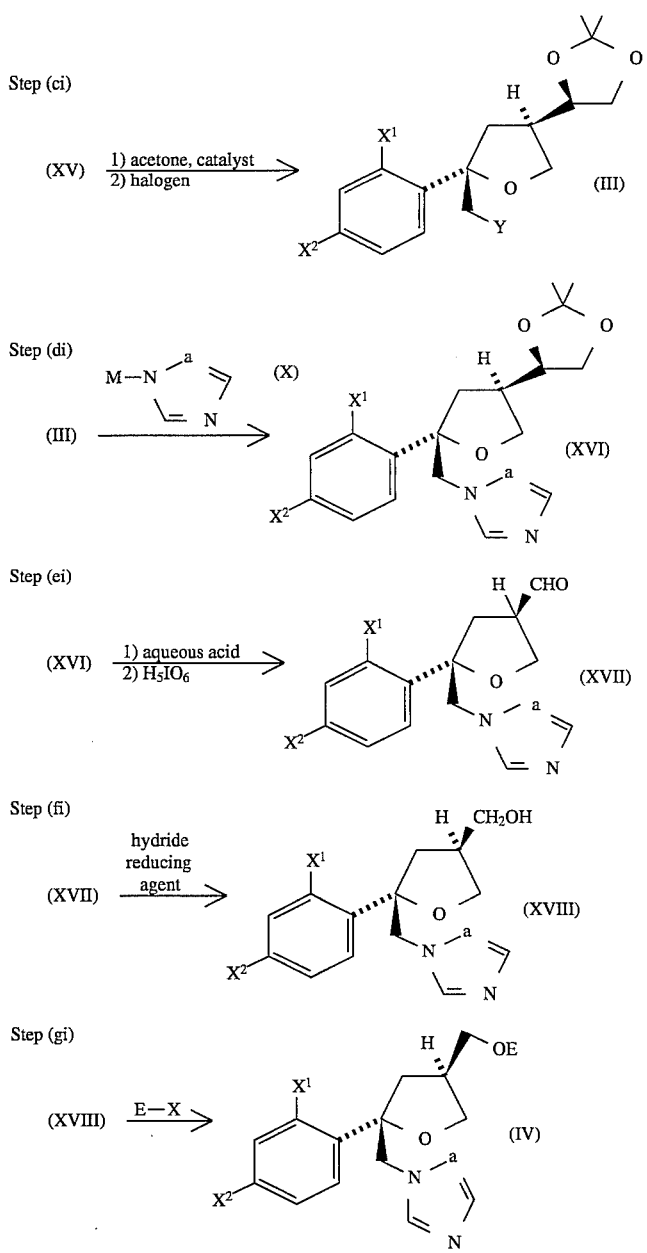

In Step (ai) of Reaction Scheme 2, a diester of D-malic acid (XIII) wherein R is $C_1$–$C_6$ alkyl, or a D-malic acid derivative of the formula (XXI) wherein R, $R^1$ and $R^2$ are as defined above, is converted to the product (XIV) or (XXII), respectively, via essentially the same procedure as described for Step (a) of Reaction Scheme 1.

Steps (bi) through (gi) are carried out via essentially the same procedures as described for Steps (b) through (g) of Reaction Scheme 1 to give compounds of formulae (III) and (IV).

Compounds of the formula (V) and (XIII) are known and can be prepared via esterification of L- or D-malic acid, respectively, using standard methods.

Compounds of the formula (XIX) and (XXI) can be prepared from L- or D-malic acid, respectively, using standard methods. For example, by reacting L- or D-malic acid with a compound of the formula

wherein $R^1$ and $R^2$ are as defined above, in the presence of an acid catalyst, such as $BF_3 \cdot OEt_2$, p-TSA, or $H_2SO_4$, in a suitable solvent, such as $CH_2Cl_2$, pentane, THF or toluene, to form a compound of the formula

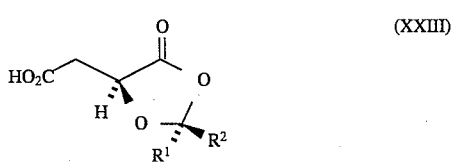

(XXIII)

-continued or

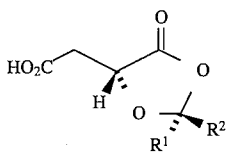

(XXIV)

respectively. The compound (XXIII) or (XXIV) is then esterified using standard methods, such as treating with diazomethane in an ether solvent, such as Et$_2$O or THF, or treating with a compound of the formula R-L, wherein R and L are as defined above, in the presence of a base to form the desired compound (XIX) or (XXI), respectively.

Compounds of the formula (XIX) or (XXI) can also be prepared from a compound of the formula (V) or (XIII), respectively, by treating (V) or (XIII) with a compound of the formula $$\underset{R^1\phantom{XX}R^2}{\overset{\overset{O}{\|}}{\diagup\!\!\diagdown}}$$

wherein R$^1$ and R$^2$ are as defined above, in the presence of an acid catalyst, such as BF$_3$·OEt$_2$, p-TSA, or H$_2$SO$_4$, in a suitable solvent, such as CH$_2$Cl$_2$, pentane, THF or toluene.

Compounds of the formula (XIX) or (XXI), wherein one of R$^1$ or R$^2$ is H and the other is —C(CH$_3$)$_3$, can also be prepared by reacting L- or D-malic acid, respectively, with [(CH$_3$)$_3$Si]$_2$NH and (CH$_3$)$_3$SiCl, followed by treatment with (CH$_3$)$_3$CCHO in the presence of TMSOTf in a suitable solvent, such as CH$_2$Cl$_2$, at −40° to 10° C., preferably at −25° to 0° C.

Compounds of the formula (VI) and (X) are known and can be readily prepared via established methods.

The following preparations and examples are illustrative of the process of the present invention.

PREPARATION 1

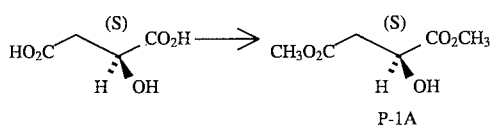

P-1A

Combine 6.7 g (50 mmol) of (−)-L-malic acid and 100 mL of MeOH, then add 0.95 g (50 mmol) of p-TSOH. Heat the mixture at reflux for 12 h., then cool to room temperature and concentrate in vacuo to a residue. Dissolve the residue in 30 mL of CH$_2$Cl$_2$ and wash with 30 mL of saturated NaHCO$_3$ (aqueous). Extract the aqueous layer with CH$_2$Cl$_2$ (3×10 mL), combine the organic phases and dry over anhydrous MgSO$_4$. Concentrate in vacuo to give 6.35 g (78% yield) of the product P-1A. MS m/z 163.2 (M+1).

Using essentially the same procedure compounds P-1B and P-1C were prepared by substituting EtOH, or iPrOH, respectively, for MeOH:

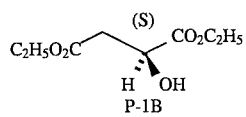

P-1B

MS m/z 191.25 (M + 1)
[α]$_D^{27}$ = −12.2°
(c = 1.0, MeOH)

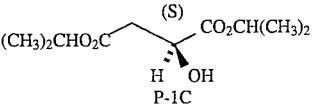

P-1C

MS m/z 219.25 (M + 1)

The (R)-isomer of compound P-1B, (e.g. compound P-1D) was also prepared from (R)-(+)-L-malic acid via essentially the same procedure:

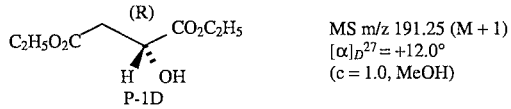

P-1D

MS m/z 191.25 (M + 1)
[α]$_D^{27}$ = +12.0°
(c = 1.0, MeOH)

PREPARATION 2

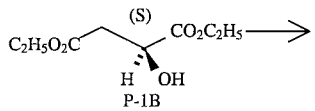

P-1B

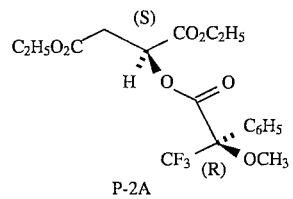

P-2A

The Enantiomeric purity of compound P-1B was determined by treating a solution of 57 mg (0.3 mmol) of compound P-1B in 0.5 mL of CH$_2$Cl$_2$ with 0.3 mL of pyridine and 101 mg (0.4 mmol) of (R)-MTPACl at 0°–10° C. Stir the mixture for 1 h. at room temperature, then add 0.5 mL of 5% HCl (aqueous). Extract the aqueous phase with CH$_2$Cl$_2$, combine the organic phases and dry over MgSO$_4$. Concentrate in vacuo to give 180 mg of the product. Analyze the product by $^1$H NMR (CDCl$_3$, 300 MHz) to determine the ratio of diastereomers: 98% (S),(R)-isomer (compound P-2A) at 3.62 ppm (doublet, J=1.16 Hz) and 2% (R),(R)-isomer (compound P-2B) 3.54 ppm, (doublet, J=1.10 Hz).

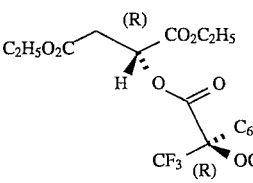

P-2B

EXAMPLE 2

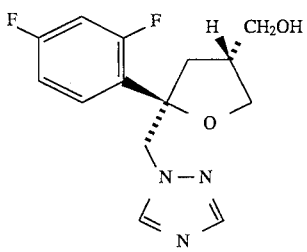

Step (a):

-continued

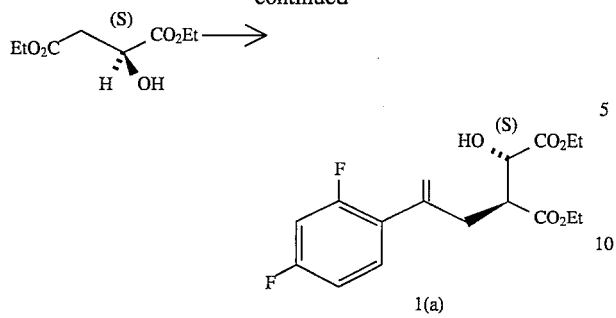

Combine 36.1 g (0.19 mole) of compound P-1B and 95 mL of THF under nitrogen atmosphere. Stir the mixture at −78° C. and slowly add (dropwise) 380 mL (0.38 mole) of a 1.0M solution of LiHMDS in THF. Stir at −78° C. for 30 min., gradually warm to −20° C., then cool to −78° C. Slowly add (dropwise) a solution of 26.6 g (95 mmol) of 2-(2',3'-difluorophenyl)-3-iodo-1-propene in 95 mL of THF. Stir at −78° C. for 30 min., then at −20° C. overnight. Warm to 0° C., then quench with 100 mL of 5% KH$_2$PO$_4$ (aqueous) and extract with 200 mL of EtOAc. Extract the aqueous phase with EtOAc 3×100 mL, combine the organic extracts and wash successively with 5% HCl (aqueous) and 100 mL of brine, then dry over MgSO$_4$. Concentrate in vacuo to give 37.6 g of a residue. Combine the residue with 5 mL of a 1M solution of (nBu)$_4$NF in THF and 10 mL of hexane, and stir for 30 min. at room temperature. Concentrate in vacuo to a residue and chromatograph (silica gel, 20% acetone in hexane) to give 27.63 g (85% yield) of the product 1(a). $[\alpha]_D^{22.8}=+18.2°$ (c=1.0, MeOH). High Resolution MS: M$^+$343.1349, theoretical 343.1357.

$^1$H NMR (CDCl$_3$, 300 MHz) shows product 1(a) is a mixture of 93% of the 2S,3S-isomer 1(a)(i) and 7% 2S,3R-isomer 1(a)(ii):

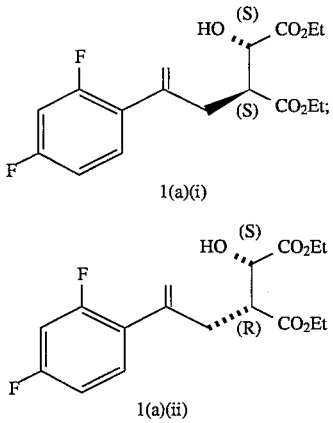

Step (b):

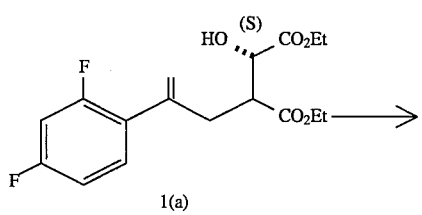

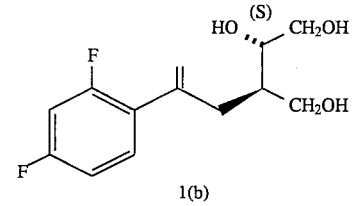

Combine 0.73 g (19.2 mmol) of NaBH$_4$, 0.80 g (19.2 mmol) of LiCl and 16 mL of 1:1 THF/water. Stir the mixture at 0° C. and add a solution of 2.75 g (8.0 mmol) of the product 1(a) from Step (a) in 2 mL of THF. Stir the mixture at room temperature for 24 h., then add 4 mL of 1N NaOH (aqueous) and stir for 16 h. Add 2 N HCl (aqueous) to acidify the mixture to pH=3–4, then extract with EtOAc (5×5 mL). Combine the organic extracts, wash with saturated K$_2$CO$_3$ (aqueous) and dry over MgSO$_4$. Concentrate in vacuo to give 1.60 g (77% yield) of the product. $[\alpha]_D^{25}=-4.1°$ (c=1.0, MeOH). MS m/z 259.2 (M+1).

$^1$H NMR (CDCl$_3$, 300 MHz) shows product 1(b) is a mixture of 94% of the 2S,3S-isomer 1(b)(i) and 6% 2S,3R-isomer 1(b)(ii):

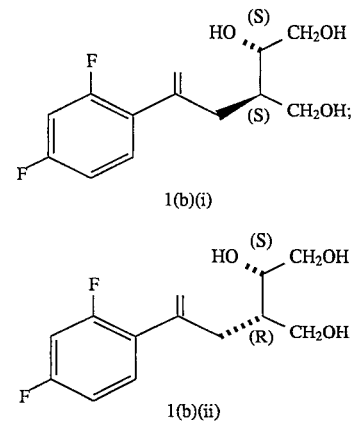

Step (c):

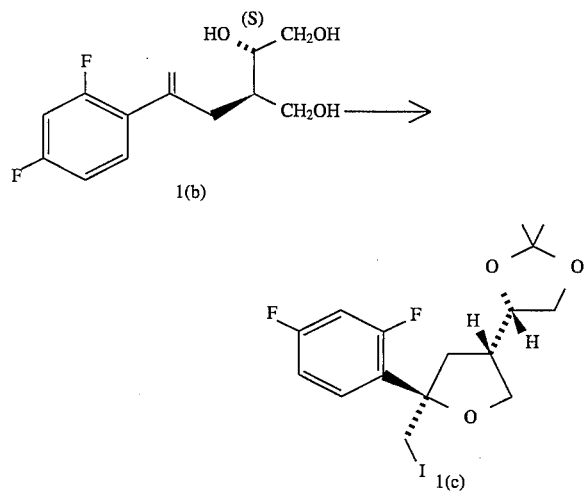

Combine 2.31 g (9.0 mmol) of compound 1(b) from Step (b), 18 mL of acetone, stir at room temperature and add 0.69 g (0.27 mmol) of I$_2$. Stir at room temperature for 4 h., then cool to −25° to −30° C. and add 3.82 g (36 mmol) of Na$_2$CO$_3$ (anhydrous). Slowly add (in eight portions) 5.67 g (22.5 mmol) of I$_2$ and stir at −25° C. for 24 h. Slowly warm to 0°

C., stir for 30 min., then add 18 mL of a 20% solution of Na₂S₂O₃ in saturated K₂CO₃ (aqueous). Extract with EtOAc (5×10 mL), combine the extracts and was with a 20% solution of Na₂S₂O₃ in saturated K₂CO₃ (aqueous). Dry over MgSO₄ and concentrate in vacuo to give a 100% yield of the product 1(c), which can be used directly in Step (d). Analysis by ¹H NMR shows the product 1(c)is 97% pure and is a 91:9 mixture of compounds 1(c)(i) and 1(c)(ii):

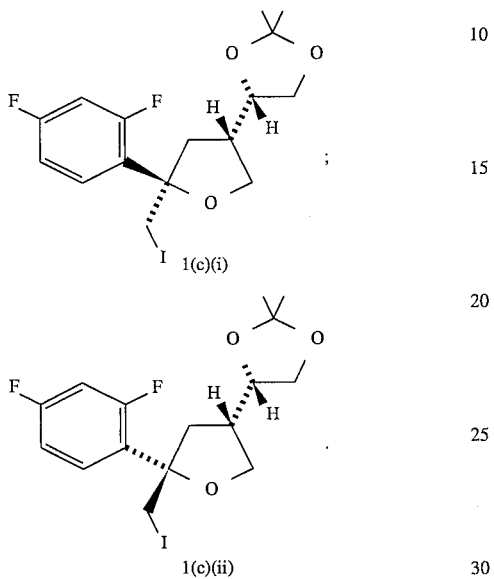

The product 1(c) is purified by chromatography (silica gel, 82:10:7:1 CH₂Cl₂/hexane/MeOH/NH₄OH) to give 3.17 g (84% yield) of compound 1(c)(i). MS m/z 425.0 (M+1).

Step (d):

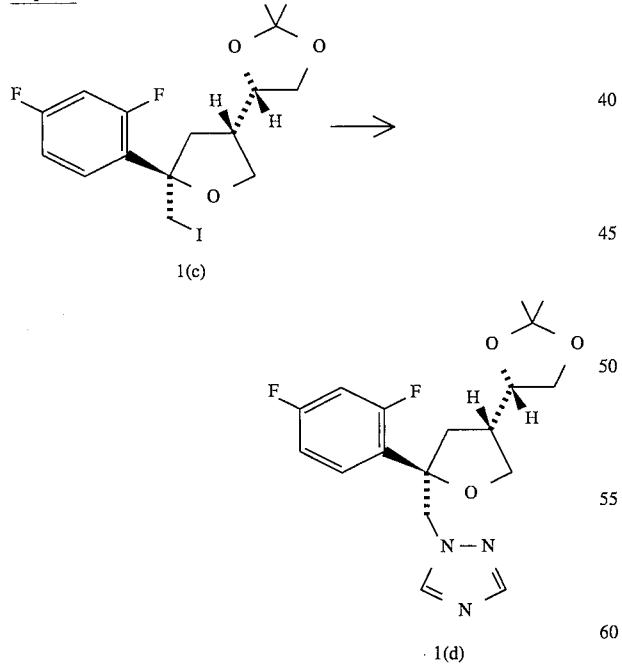

Combine 2.54 g (6.0 mmol) of the product 1(c) of Step (c), 6 mL of DMSO and 1.64 g (18 mmol) of sodium 1,3,4-triazole. Stir the mixture at 100°–105° C. for 24 h., then cool to room temperature. Partition between 24 mL of water and 6 mL of EtOAc. Extract the aqueous layer with EtOAc (5×3 mL), combine the organic phases, wash with brine and dry over MgSO₄. Concentrate in vacuo to a residue and purify by chromatography (silica gel, 82:10:7:1 CH₂Cl₂/hexane/MeOH/NH₄OH) to give 1.56 g (69% yield) of the product 1(d). MS m/z 366.4 (M+1). The product 1(d)is a 90:10 mixture of the compounds 1(d)(i) and 1(d)(ii):

Step (e):

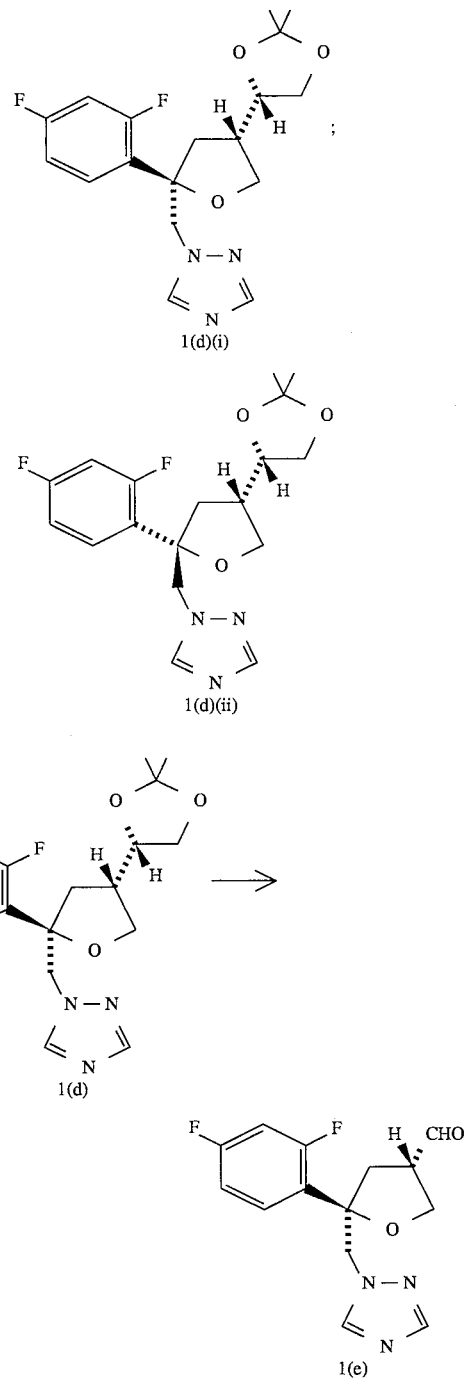

Combine 0.78 g (2.13 mmol) of the product 1(d) from Step (d), 2.1 mL of THF and 2.1 mL of 1N HCl (aqueous), and stir at room temperature for 3 h. Add 0.73 g (3.2 mmol) of H₅IO₆ and stir for 24 h. Add 8 mL of a 20% solution of Na₂S₂O₃ in saturated K₂CO₃ (aqueous), then dilute with 4 mL of water. Extract with EtOAc (5×10 mL), combine the extracts and wash with a 20% solution of Na₂S₂O₃ in saturated K₂CO₃ (aqueous). Dry over MgSO₄, then concentrate in vacuo to a residue. Purify the residue by chromatography (silica gel, 5% MeOH in CH$_2$Cl$_2$) to give 0.49 g (79% yield) of the product 1(e). MS m/z 294.1 (M+1). The product 1(e) is a 90:10 mixture of the compounds 1(e)(i) and 1(e)(ii):

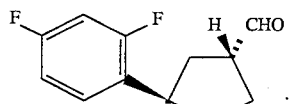

1(e)(i)

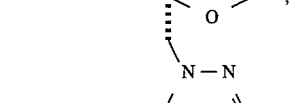

1(e)(ii)

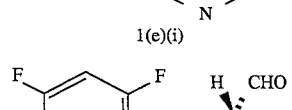

1(e)

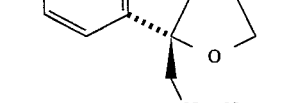

1(f)

Combine 0.40 g (1.36 mmol) of the product 1(e) from Step (e) and 2.7 mL of MeOH, then cool to 10° C. and add 0.052 g (1.36 mmol) of NaBH$_4$. Stir the mixture for 1 h., then add 1 mL of 1N NaOH (aqueous) and stir for 15 min. Extract with EtOAc (5×2 mL), combine the extracts, wash with saturated K$_2$CO$_3$ (aqueous) and dry over MgSO$_4$. Concentrate in vacuo to give 0.40 g (100% yield) of the product 1(f). MS m/z 296.1 (M+1). [α]$_D^{27}$=−48.8° (c=0.85, CHCl$_3$). $^1$H NMR analysis (CDCl$_3$, 300 MHz) shows that product 1(f) is 94% of the R,R-isomer 1(f)(ii) and 6% of the R,S-isomer 1(f)(i):

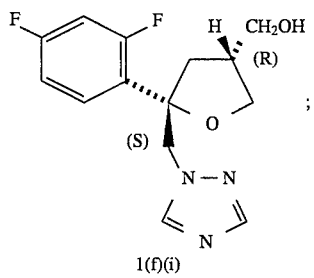

1(f)(i)

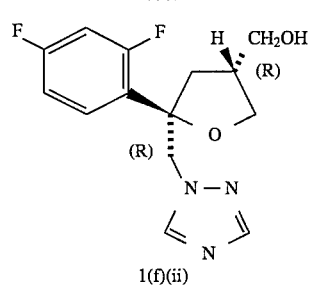

1(f)(ii)

EXAMPLE 2

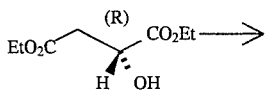

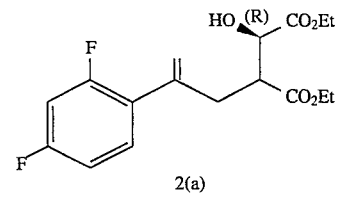

2(a)

Following essentially the same procedure as described in Example 1, Step (a), and using 2.85 g (15 mole) of compound P-1D, and corresponding amounts of the other reagents, 1.93 g (75% yield) of the product 2(a) was prepared. [α]$_D^{25}$=−14.54° (c=1.0, MeOH). MS (m/z)=343.2 (M+1).

$^1$H NMR (CDCl$_3$, 300 MHz) shows that the product 2(a) is a mixture of 94% of the 2R,3R-isomer 2(a)(i) and 6% 2R,3S-isomer 2(a)(ii):

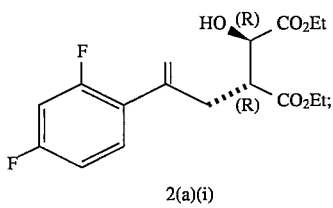

2(a)(i)

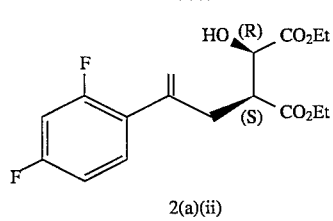

2(a)(ii)

EXAMPLE 3

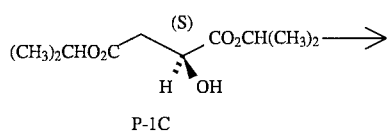

P-1C

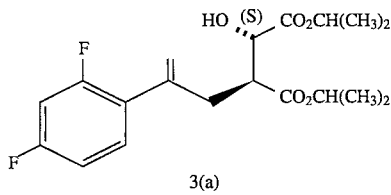

3(a)

The product P-1C prepared according to Preparation 1 (65 mg, 0.3 mmol) is treated with 84 mg of 2-(2',3'-difluorophenyl)-3-iodo-1-propene and 0.93 mmol of LiHMDS by essentially the same procedure as described in Example 1, Step (a) to give 67 mg (60% yield) of the product 3(a). MS m/z 371.4 (M+1).

EXAMPLE 4

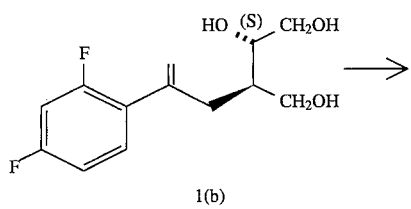

1(b)

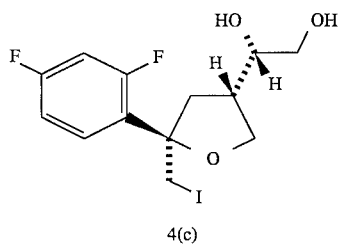

4(c)

Combine 28 mg (0.1 mmol) of the product 1(b) from Example 1, Step (b) and 0.2 mL of $CH_3CN$, stir the mixture, then add 42 mg (0.4 mmol) of $Na_2CO_3$. Cool the mixture to −25° to −20° C., add 63 mg (0.25 mmol) of Iodine and stir at −25° C. for 3h. Slowly warm the mixture to 0° C. and stir for 6 h., then quench with 0.5 mL of 20% $Na_2S_2O_3$ in saturated $K_2CO_3$ (aqueous). Extract with EtOAc (5×2 mL) and wash the combined extracts with 20% $Na_2S_2O_3$ in saturated $K_2CO_3$ (aqueous). Dry the combined extracts over $MgSO_4$ and concentrate in vacuo to give 40 mg (96% yield) of the diol product 4(c). MS m/z 385.1 (M+1), 367.1 (M+1−$H_2O$), 349.1 (M+1−2$H_2O$). (The product is an 85:15 mixture of cis to trans isomers by $^1H$ NMR.)

EXAMPLE 5

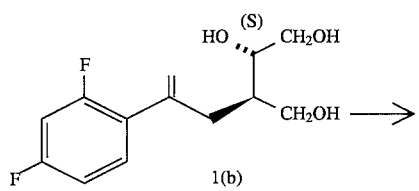

1(b)

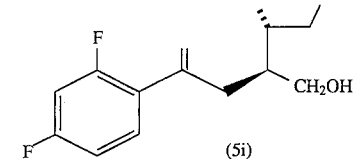

(5i)

Combine 0.102 g (0.4 mmol) of the product 1(b) from Example 1, Step (b) and 0.5 mL of acetone. Cool the mixture at −30° to −25° C., add 2.1 mg (0.008 mmol) of 12, then stir at −25° C. for 4 h. Add $Na_2S_2O_3$ (about 0.05 g) stir for 30 min., then warm to room temperature and filter through celite®. Concentrate the flitrate to give 78 mg of the ketal product 5(i). MS m/z 385.1 (M+1). The product is a 87:13 mixture of 5(i) and its regioisomer 5(ii) by $^1H$ NMR

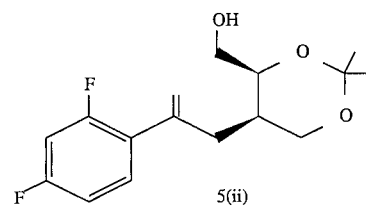

5(ii)

EXAMPLE 6

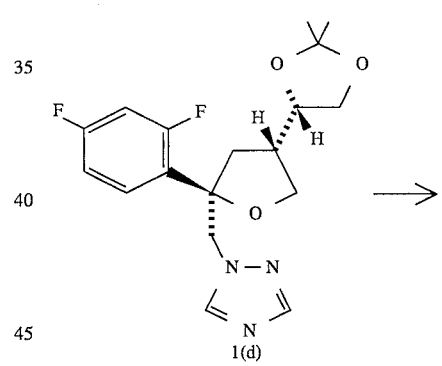

1(d)

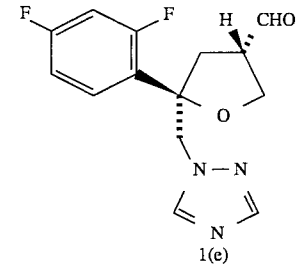

1(e)

Combine 50 mg (0.13 mmol) of the product 1(d) from Step (d), 0.4 mL of 1:1 MeOH/water and 45 mg (0.2 mmol) of $H_5IO_6$. Stir the mixture at room temperature for 4 h., then quench with 2 mL of saturated $K_2CO_3$ (aqueous). Extract with EtOAc (5×2 mL), combine the extracts and wash with a 20% solution of $Na_2S_2O_3$ in saturated $K_2CO_3$ (aqueous). Dry over MgSO, then concentrate in vacuo to give 33 mg (82% yield) of the aldehyde product 1(e). MS m/z 294.3 (M+1).

EXAMPLE 7

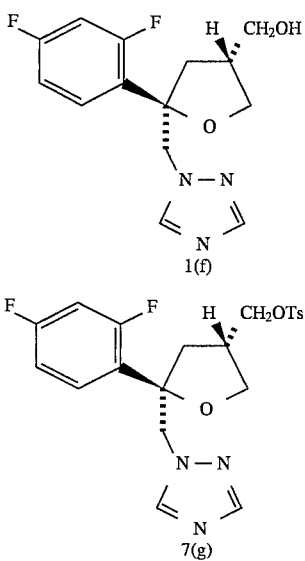

Combine 0.182 g (0.61 mmol) of the product 1(f) of Example 1, Step (f), and 0.6 mL of THF. Add 0.3 mL of 25% NaOH (aqueous) and 0.174 g (0.92 mmol) of TsCl. Stir the resulting biphasic mixture at room temperature for 4 h., then add 0.85 g of TsCl and stir for 18 h. Separate the layers and extract the aqueous layer with TBME (4×5 mL), Combine the organic layer and the extracts and wash with saturated $Na_2CO_3$ (aqueous). Dry over $MgSO_4$ and concentrate in vacuo to a residue. Chromatograph the residue (silica gel, TBME) to give 0.08 g (76% yield) of the rosylate product 7(g). MS m/z 450.0 (M+1).

EXAMPLE 8

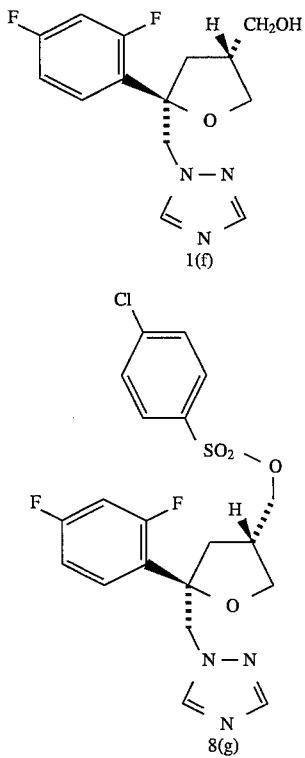

Combine 0.32 g (1.1 mmol) of the product 1(f) of Example 1, Step (f), and 2.2 mL of $CH_2Cl_2$. Add 0.32 mL (2.3 mmol) of $Et_3N$ and 0.33 g (1.54 mmol) of 4-chlorobenzenesulfonyl chloride and stir the mixture at room temperature for 18 h. Add 5 mL of 25% NaOH (aqueous) and stir for 1 h. Chill to 0° to 5° C. and slowly add 4M $H_2SO_4$ (aqueous) to bring the mixture to pH 6–8. Separate the layers and extract the aqueous layer with $CH_2Cl_2$ (4×5 mL). Combine the organic phases and wash with saturated $Na_2CO_3$ (aqueous). Dry over $MgSO_4$ and concentrate in vacuo to a residue. Chromatograph the residue (silica gel, EtOAc) to give 0.38 g (76% yield) of the product 8(g). MS m/z 470.0 (M+1).

We claim:

1. A process for preparing chiral compounds of the formula

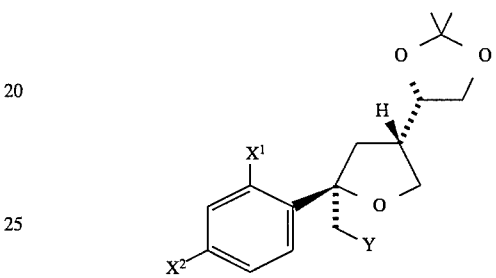

wherein $X^1$ and $X^2$ are independently F or Cl, and Y is Cl, Br or I, comprising reacting a triol of the formula

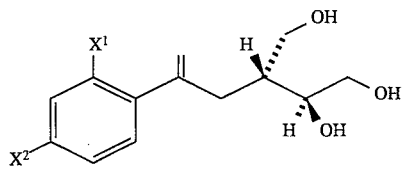

wherein $X^1$ and $X^2$ are as defined above, with acetone in the presence of a catalyst, then with a halogen selected from $Cl_2$, $Br_2$ or $I_2$, or N-bromosuccinimide or N-iodosuccinimide.

2. The process of claim 1 wherein $X^1$ and $X^2$ are both F, Y is I, and the halogen is $I_2$.

3. The process of claim 2 wherein the catalyst is $I_2$.

4. The process of claim 3 wherein the treatment with halogen is carried out in the presence of a moderate base at a temperature of −50° to 25° C.

5. The process of claim 4 wherein the moderate base is $Na_2CO_3$ or $K_2CO_3$ and the temperature is −30° to 0° C.

6. A process for preparing chiral compounds of the formula

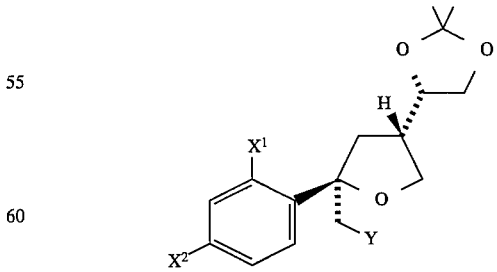

wherein $X^1$ and $X^2$ are independently F or Cl, and Y is Cl, Br or I, comprising the steps:

(a) using a nonaqueous base to deprotonate a chiral compound of the formula

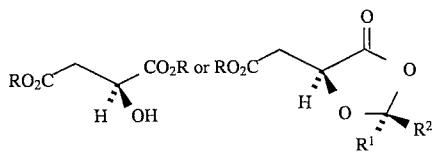

wherein: R is $C_1$–$C_6$ alkyl;
one of $R^1$ or $R^2$ is H and the other is —$C(CH_3)_3$ or —$CCl_3$, or $R^1$ and $R^2$ are both $C_1$–$C_6$ alkyl, or $R^1$ and $R^2$ together with the carbon to which they are attached comprise a 6-membered carbocyclic ring, then treating with a compound of the formula

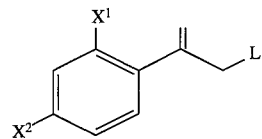

wherein $X^1$ and $X^2$ are as defined above and L is a leaving group, to form a chiral compound of the formula

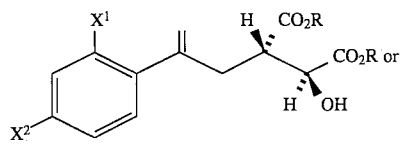

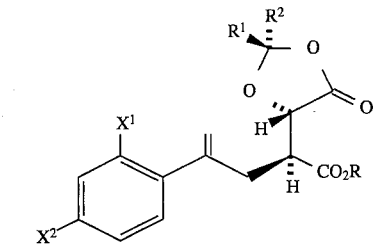

respectively, wherein $X^1$, $X^2$, R, $R^1$ and $R^2$ are as defined above;

(b) reducing the product of step (a) with a hydride reducing agent to form a chiral triol of the formula

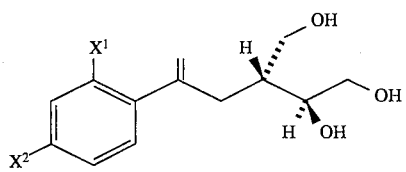

wherein $X^1$ and $X^2$ are as defined above; and (c) reacting the triol of step (b) with acetone in the presence of a catalyst, then with a halogen selected from $Cl_2$, $Br_2$ or $I_2$, or N-bromosuccinimide or N-iodosuccinimide.

7. The process of claim 6 wherein: $X^1$ and $X^2$ are both F; L is I; R is methyl, ethyl or i-propyl; the nonaqueous base is $LiN[Si(CH_3)_3]_2$; the hydride reducing agent is $LiBH_4$ or a mixture of $NaBH_4$ and LiCl; the catalyst in step (c) is $I_2$; and the halogen is $I_2$.

8. A process for preparing a compound of the formula

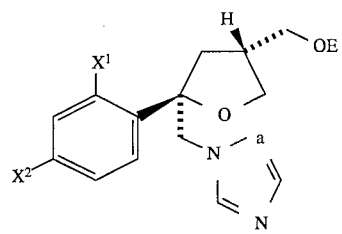

wherein: a is CH or N; $X^1$ and $X^2$ are independently F or Cl; and E is —$SO_2R^6$, wherein $R^6$ is $C_1$–$C_6$ alkyl, $CF_3$, aryl, or substituted aryl, wherein said substituted aryl is an aryl group having 1 to 3 substituents selected from halogeno, $C_1$–$C_6$ alkyl, $NO_2$ and $CF_3$, comprising the steps:

(a) using a nonaqueous base to deprotonate a chiral compound of the formula

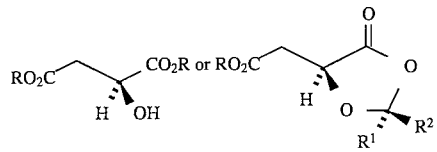

wherein: R is $C_1$–$C_6$ alkyl;
one of $R^1$ or $R^2$ is H and the other is —$C(CH_3)_3$ or —$CCl_3$, or $R^1$ and $R^2$ are both $C_1$–$C_6$ alkyl, or $R^1$ and $R^2$ together with the carbon to which they are attached comprise a 6-membered carbocyclic ring, then treating with a compound of the formula

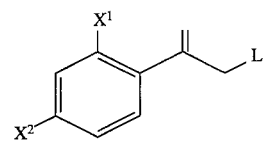

wherein $X^1$ and $X^2$ are as defined above and L is a leaving group, to form a chiral compound of the formula

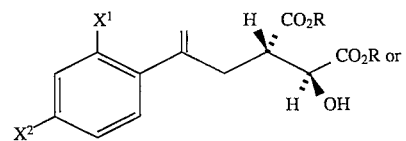

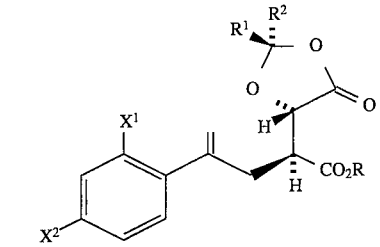

respectively, wherein $X^1$, $X^2$, R, $R^1$ and $R^2$ are as defined above;

(b) reducing the product of step (a) with a hydride reducing agent to form a chiral triol of the formula

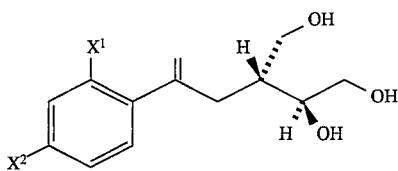

wherein $X^1$ and $X^2$ are as defined above;

(c) reacting the triol of step (b) with acetone in the presence of a catalyst, then with a halogen selected from $Cl_2$, $Br_2$ or $I_2$, or N-bromosuccinimide or N-iodosuccinimide, to form a chiral tetrahydrofuran of formula

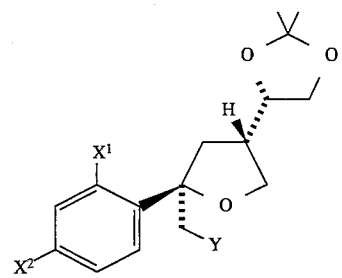

wherein $X^1$ and $X^2$ are as defined above and Y is Cl, Br or I;

(d) treating the tetrahydrofuran of step (c) with an alkali metal triazole or imidazole to form a chiral triazole or imidazole compound of the formula

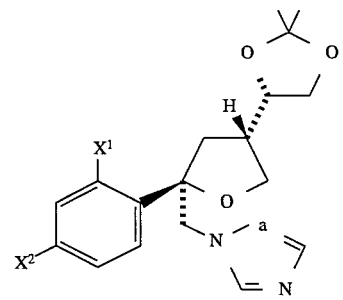

wherein a, $X^1$ and $X^2$ are as defined above;

(e) hydrolyzing the triazole or imidazole product of step(d) with an aqueous acid to form a diol intermediate of the formula

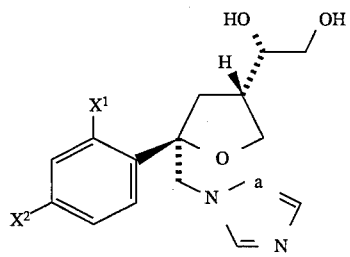

followed by oxidatively cleaving the diol using $H_5IO_6$, $NaIO_4$ or $Pb(OAc)_4$ to form an aldehyde of the formula

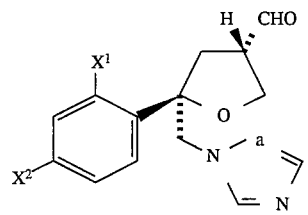

wherein a, $X^1$ and $X^2$ are as defined above;

(f) reducing the aldehyde of step (e) with a hydride reducing agent to form an alcohol of the formula

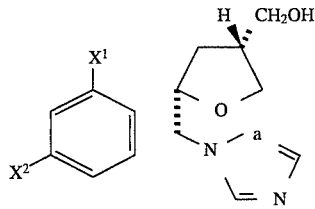

wherein a, $X^1$ and $X^2$ are as defined above; and (g) treating the alcohol of step (f) with a compound of the formula E-X, wherein X is Cl or Br, and E is as defined above.

9. The process of claim 8 wherein: a is N; $X^1$ and $X^2$ are both F; L is I; R is methyl, ethyl or i-propyl; in step (a) the nonaqueous base is $LiN[Si(CH_3)_3]_2$; in step (b) the hydride reducing agent is $LiBH_4$ or a mixture of $NaBH_4$ and LiCl; n step (c) the catalyst is $I_2$, and the halogen is $I_2$, and Y is I; in step (d) the alkali metal triazole is sodium triazole; in step (e) the aqueous acid is aqueous HCl; in step (f) the hydride reducing agent is $NaBH_4$; and in step (g) E is $CH_3C_6H_4SO_2-$ or $ClC_6H_4SO_2-$ and X is Cl.

10. The process of claim 9 wherein: step (a) is carried out in tetrahydrofuran at a temperature of $-100°$ to $0°$ C.; step (b) is carried out in an organic water miscible solvent in the presence of water; in step (c) the treatment with halogen is carried out in the presence of a moderate base at a temperature of $-50°$ to $25°$ C.; step (d) is carried out at $50°$ to $150°$ C. in N,N-dimethylformamide or dimethylsulfoxide; step (e) is carried out in tetrahydrofuran at $0°$ to $50°$ C.; step (f) is carried out in an organic water miscible solvent at $-30°$ to $50°$ C.; and step (g) is carried out in the presence of a base and a solvent selected tetrahydrofuran or $CH_2Cl_2$.

11. The process of claim 10 wherein: in step (b) the water miscible solvent is tetrahydrofuran; in step (c) the moderate base is $Na_2CO_3$; in step (f) the water miscible solvent is MeOH; and in step (g) the base is pyridine or NaOH.

12. A process for preparing an enantiomer of a compound of claim 6 comprising (ai) using a nonaqueous base to deprotonate a chiral compound of the formula

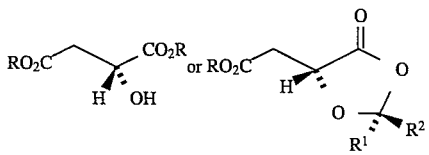

wherein: R is $C_1-C_6$ alkyl;

one of $R^1$ or $R^2$ is H and the other is $-C(CH_3)_3$ or $-CCl_3$, or $R^1$ and $R^2$ are both $C_1-C_6$ alkyl, or $R^1$ and $R^2$ together with the carbon to which they are attached comprise a 6-membered carbocyclic ring, then treating with a compound of the formula

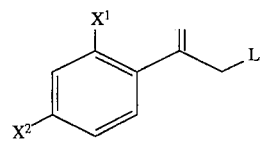

wherein $X^1$ and $X^2$ are as defined above and L is a leaving group, to form a chiral compound of the formula

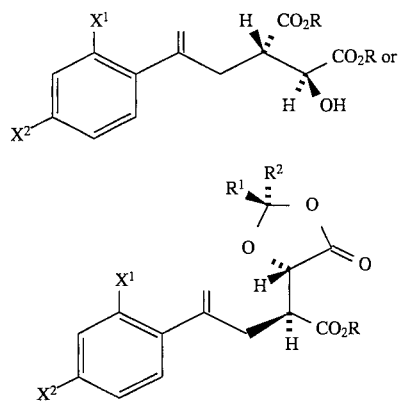

respectively, wherein $X^1$, $X^2$, R, $R^1$ and $R^2$ are as defined above; and (bi) sequentially treating the product of step (ai) as described in steps (b) and (c) of claim 6 to give the enantiomer having the formula

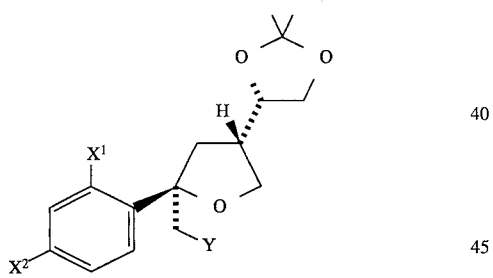

wherein $X^1$, $X^2$ and Y are as defined in claim 6.

13. The process of claim 12 wherein: $X^1$ and $X^2$ are both F; L is I; R is methyl, ethyl or i-propyl; the nonaqueous base is $LiN[Si(CH_3)_3]_2$; the hydride reducing agent is $LiBH_4$ or a mixture of $NaBH_4$ and LiCl; the catalyst in step (c) is $I_2$; and the halogen is $I_2$.

14. A process for preparing an enantiomer of a compound of claim 8 comprising:

(ai) using a nonaqueous base to deprotonate a chiral compound of the formula

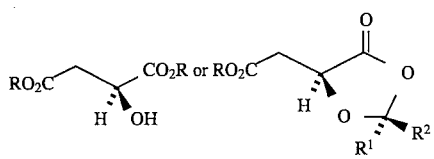

wherein: R is $C_1$-$C_6$ alkyl;

one of $R^1$ or $R^2$ is H and the other is —$C(CH_3)_3$ or —$CCl_3$, or $R^1$ and $R^2$ are both $C_1$-$C_6$ alkyl, or $R^1$ and $R^2$ together with the carbon to which they are attached comprise a 6-membered carbocyclic ring, then treating with a compound of the formula

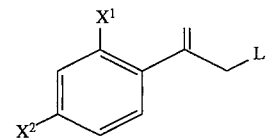

wherein $X^1$ and $X^2$ are as defined above and L is a leaving group, to form a chiral compound of the formula

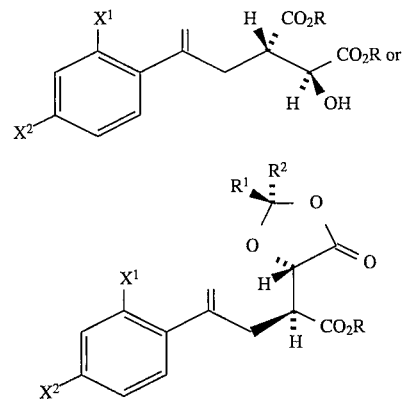

respectively, wherein $X^1$, $X^2$, R, $R^1$ and $R^2$ are as defined above; and (bi) sequentially treating the product of step (ai) as described in steps (b), (c), (d), (e), (f) and (g) of claim 8 to form an enantiomer of the formula

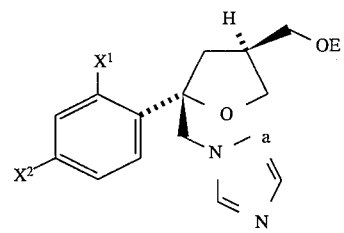

wherein: a is CH or N; $X^1$ and $X^2$ are independently F or Cl; and E is —$SO_2R^6$, wherein $R^6$ is $C_1$-$C_6$ alkyl, aryl, substituted aryl or —$CF_3$.

15. The process of claim 14 wherein: a is N; $X^1$ and $X^2$ are both F; L is I; R is methyl, ethyl or i-propyl; in step (a) the nonaqueous base is $LiN[Si(CH_3)_3]_2$; in step (b) the hydride reducing agent is $LiBH_4$ or a mixture of $NaBH_4$ and LiCl; n step (c) the catalyst is $I_2$, and the halogen is $I_2$, and Y is I; in step (d) the alkali metal triazole is sodium triazole; in step (e) the aqueous acid is aqueous HCl; in step (f) the hydride reducing agent is $NaBH_4$; and in step (g) E is $CH_3C_6H_4SO_2$— or $ClC_6H_4SO_2$— and X is Cl.

16. The process of claim 15 wherein: step (a) is carried out in tetrahydrofuran at a temperature of −100° to 0° C.; step (b) is carried out in an organic water miscible solvent in the presence of water; in step (c) the treatment with halogen is carried out in the presence of a moderate base at a temperature of −50° to 25° C.; step (d) is carried out at 50° to 150° C. in N,N-dimethylformamide or dimethylsulfoxide; step (e) is carried out in tetrahydrofuran at 0° to 50° C.; step (f) is carried out in an organic water miscible solvent at −30° to 50° C.; and step (g) is carried out in the presence of a base and a solvent selected tetrahydrofuran or $CH_2Cl_2$.

17. The process of claim 16 wherein: in step (b) the water miscible solvent is tetrahydrofuran; in step (c) the moderate base is $Na_2CO_3$; in step (f) the water miscible solvent is MeOH; and in step (g) the base is pyridine or NaOH.

* * * * *

UNITED STATES PATENT AND TRADEMARK OFFICE
CERTIFICATE OF CORRECTION

PATENT NO.   :   5,486,625                                          Page 1 of 2
DATED        :   January 23, 1996
INVENTOR(S)  :   William Leong, Lyman H. Smith It is certified that error appears in the above-identified patent and that said Letters Patent is hereby corrected as shown below:

Column 16, line 54, cancel "EXAMPLE 2" and insert --EXAMPLE 1--.
Column 21, line 28, insert --Step (f)--; line 35, insert an arrow -- → -- after the formula.
Column 25, lines 8 and 43, insert an arrow -- → -- after each formula.
Column 29, line 30, "1" should read --I--; line 66, "$H_5IO_6$" should read --$H_5IO_6$--; line 67, "$NaIO_4$" should read --$NaIO_4$--.
Column 30 lines 13 to 23, the formula should read

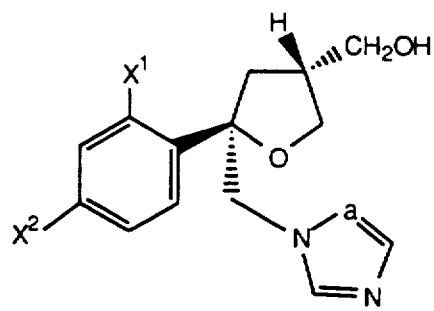

Column 31, lines 13 to 18, that portion of the formula reading

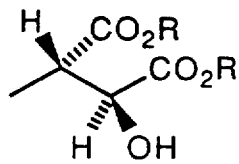 should read 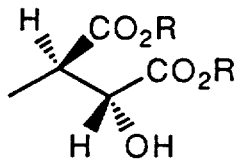 ; and lines 20 to 28, that portion of the formula reading 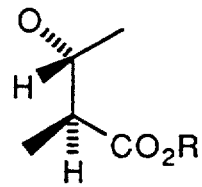 should read 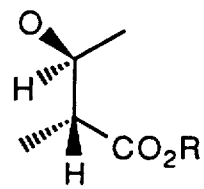

UNITED STATES PATENT AND TRADEMARK OFFICE
CERTIFICATE OF CORRECTION

PATENT NO.    : 5,486,625
DATED         : January 23, 1996
INVENTOR(S)   : William Leong, Lyman H. Smith It is certified that error appears in the above-identified patent and that said Letters Patent is hereby corrected as shown below:

Column 31, lines 60 to 65, that portion of each formula reading 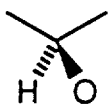 should read  .

Column 32, lines 17 to 22, that portion of the formula reading 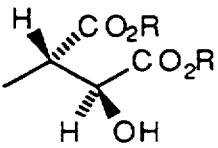 should read 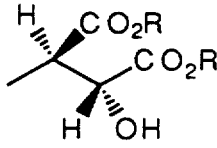 ; and lines 23 to 32, that portion of the formula reading 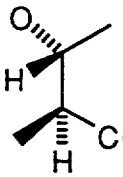 should read 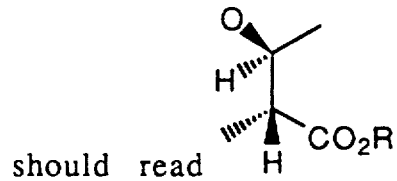

Signed and Sealed this

Thirtieth Day of April, 1996

*Attest:*

BRUCE LEHMAN

*Attesting Officer*      *Commissioner of Patents and Trademarks*